United States Patent [19]

Eagan et al.

[11] Patent Number: 5,323,655

[45] Date of Patent: Jun. 28, 1994

[54] METHOD AND APPARATUS FOR COMPACTING MATERIAL SAMPLES

[75] Inventors: John T. Eagan, Cary; Donald K. McAlister, Apex; David H. Minshall, Durham, all of N.C.

[73] Assignee: Troxler Electronic Laboratories, Inc., Research Triangle Park, N.C.

[21] Appl. No.: 52,558

[22] Filed: Apr. 23, 1993

[51] Int. Cl.⁵ .......................................... G01D 27/00
[52] U.S. Cl. ...................................... 73/432.1; 73/84
[58] Field of Search ................ 73/819, 794, 796, 798, 73/813, 432.1, 84, 146; 164/207, 211

[56] References Cited

U.S. PATENT DOCUMENTS

| | | | |
|---|---|---|---|
| 2,360,059 | 10/1944 | Hohwart | 73/7 |
| 2,471,227 | 5/1949 | Marshall | 73/821 |
| 2,531,388 | 11/1950 | Black | 73/84 X |
| 2,909,826 | 10/1959 | McElroy | 425/421 |
| 2,972,249 | 2/1961 | McRae et al. | 425/421 |
| 2,980,978 | 4/1961 | Marshall | 73/811 |
| 3,161,044 | 12/1964 | Harrison et al. | 73/769 |
| 3,404,557 | 10/1968 | Hechet et al. | 73/7 |
| 3,426,404 | 2/1969 | Yamasita et al. | 425/421 |
| 3,461,717 | 8/1969 | Dunlap et al. | 73/84 |
| 3,478,572 | 2/1969 | McRae et al. | 425/421 |
| 3,494,172 | 2/1970 | Juve et al. | 73/9 |
| 3,557,267 | 1/1971 | Angelotti et al. | 73/15 |
| 3,616,685 | 11/1971 | Strom | 73/819 |
| 3,712,785 | 1/1973 | Hirt et al. | 425/421 |
| 3,743,468 | 7/1973 | Helmrich et al. | 425/421 |
| 3,756,762 | 9/1973 | Maugweiler | 425/421 |
| 3,767,351 | 10/1973 | Blaser | 425/432 |
| 3,781,156 | 12/1973 | Moore | 425/424 |
| 3,883,278 | 5/1975 | Hass | 425/421 |
| 3,907,474 | 9/1975 | Blaser et al. | 425/421 |
| 3,932,100 | 1/1976 | Blinheim | 425/421 |
| 4,137,757 | 2/1979 | Kovacs | 73/818 |
| 4,140,744 | 2/1979 | Karas et al. | 425/421 |
| 4,179,258 | 12/1979 | Karas et al. | 425/421 |
| 4,226,820 | 10/1980 | Bjoorhaag | 425/421 |
| 4,421,471 | 12/1983 | Vogt | 425/421 |
| 4,518,335 | 5/1985 | Pujari | 425/421 |
| 4,616,508 | 10/1986 | Jorn | 73/825 |
| 4,794,799 | 1/1989 | Paakkinen | 73/803 |
| 4,885,941 | 12/1989 | Vardoulakis et al. | 73/319 |
| 4,942,768 | 7/1990 | McRae | 73/795 |
| 5,036,709 | 8/1991 | McRae | 73/841 |

FOREIGN PATENT DOCUMENTS 2728181  1/1979  Fed. Rep. of Germany .

OTHER PUBLICATIONS

"bulletin de liaison des laboratoires des ponts et chaussées, " *Ministere de L'Equipement*, No. 88, Mars-Avril 1977, pp. 132-136.

"Formulation des enrobés Bilan des essais à la presse à cisaillement giratoire (PCG)," *Bitumes et enrobes bitumineux*, pp. 13-21.

"Evaluation Methods for Properties of Bituminous Mixtures, " *T.R.B-1986*, J. Bonnot, Technical Director of the Public Works National Research Laboratory, Paris, (France), Session No., 135, pp. 1-6.

*Primary Examiner*—Jerry W. Myracle
*Attorney, Agent, or Firm*—Bell, Seltzer, Park & Gibson

[57] ABSTRACT

An apparatus and method for compacting a material sample, such as soil or paving material, including a mold for receiving the material sample and a ram mounted for movement into a first open end of the mold to provide an axial compressire force thereto. The compacting apparatus also includes a base for supporting a second end of the mold. In operation, the mold is gyrated simultaneously with the application of the axial compressire force by the ram. Gyration is provided by tilting the mold from an initial neutral position in which the center longitudinal axis of the mold is collinear with the axis of compression to a tilted operative position in which the central longitudinal axis of the mold is angularly offset from the axis of compression. The base is thereinafter rotated relative to the mold so as to revolve the center of the second end of the mold about the axis of compression, thus, gyrating the axially compressed material sample. Such simultaneous gyration and axial compression simulates the rolling of a vehicle tire or other compaction device over a material surface.

46 Claims, 4 Drawing Sheets

OTHER PUBLICATIONS

"Forecasting the Compactability of Bitumen-Coated Materials with the Aid of the Gyratory Shear Compacting Press (PCG)", translation of Francis Moutier article, *Bull. Liaison Labo. P. et Ch.*, 121, Sep.-Oct. 1982, pp. 29-32.

"Utilisations et possibilitiés de la presse à cisaillement giratoire," F. Moutier, *Bull. Liaison Labo. P. et Ch., special v*, Dec. 1977, pp. 173-180.

"La presse à cisaillement giratoire," F. Moutier, *Bull. Liaison Labo. P. et Ch.*, 68, Nov.-Dec. 1973-Ref. 1357, pp. 141-152.

"La presse à cisaillement giratoire Modéle, de série," F. Moutier, *Bull. Liaison Labo,* P et Ch.-74-Nov.-Dec. 1974, Ref. 1498, pp. 137,148.

"Press designed to study the compactness of bituminous mixes," *Gyrtory Shear Compacting Press*, Materials des Laboratories des Ponts Chaussees, 2 page brochure.

"Gyratory Testing Machine Technical Manual," Soiltest, Inc., pp. 1-94.

Fig. 2.

METHOD AND APPARATUS FOR COMPACTING MATERIAL SAMPLES

FIELD OF THE INVENTION

This invention relates to a materials testing apparatus and method, and more particularly an apparatus and method for compacting samples of paving material into standardized specimens for analysis.

BACKGROUND OF THE INVENTION

In order to measure physical properties of soils or paving materials, such as density, moisture content and compressire strength, loose samples of the soil or paving material are formed into compacted test specimens under reproducible conditions using laboratory compaction machines.

Laboratory compaction machines employing tamping as the compaction method are illustrated in U.S. Pat. No. 2,980,978 to Marshall (hereinafter the "'978 patent"). The apparatus of the '978 patent employs repetitive tamps to axially compress a sample of soil or paving material. The tamps are provided by a hamer which repetitively impacts the sample. The compaction provided by the apparatus of the '978 patent, however, is solely limited to axial compaction.

In addition compaction machines which provide axial compression while gyrating the sample of soil or paving material so as to effectively knead the sample are illustrated in U.S. Pat. Nos. 2,972,249, 3,478,572, 4,942,768 and 5,036,709 to McRae (hereinafter the "'249, '572, '768 and '709 patents", respectively) as well as a publication entitled *Gyratory Shear Compacting Press* By Materials des Laboratoires des Ponts et Chaussees (hereinafter the "MLPC publication"). The gyratory action, in conjunction with the axial compression of the sample, more closely simulates actual road conditions in which vehicle tires or other compaction device roll over the pavement. The McRae patents as well as the MLPC publication disclose a laboratory compaction apparatus for compressing a sample along an axis of compression while gyrating the confined sample. The gyratory effect is provided by an angular offset of the axis of compression from the central longitudinal axis of the mold which confines the sample during its gyration.

In particular, the '249 and '572 patents as well as the MLPC publication disclose a compaction apparatus utilizing a pair of oppositely disposed hydraulically actuated rams for axially compacting the sample. The use of two hydraulically actuated rams requires duplicative hydraulic systems which accordingly increases the complexity of the system as well as the likelihood of malfunctions in the hydraulic system, such as leaks in the hydraulic lines.

Furthermore, the gyrating mechanism for the compaction apparatuses disclosed by the '249 and '572 patents includes two oppositely disposed rollers mounted adjacent opposing faces of a outwardly extending flanged upper lip of the rotating mold. This gyrating mechanism and its associated drive means are mounted above the mold containing the specimen. The position of the gyratory mechanism above the mold may increase the difficulty of loading and unloading of the specimen and the mold. In addition, safety procedures must be rigidly adhered to by the operator to insure that all personnel are clear of the mold and gyratory mechanism prior to commencing compaction.

SUMMARY OF THE INVENTION

It is therefore an object of the present invention to provide an apparatus and method for compacting materials.

It is another object of the present invention to provide an apparatus and method for axially compacting materials while simultaneously gyrating the material sample.

It is still another object of the present invention to provide an apparatus and method for compacting materials along an axis of compression while simultaneously gyrating the material sample at a predetermined angular offset from the axis of compression.

These and other objects are provided according to the present invention by a material sample compacting apparatus having a mold for receiving and confining the material sample to be compacted, a compression means for axially compacting the confined material sample and a base assembly for supporting and gyrating the mold and its confined material sample. Additionally, the mold is preferably cylindrical.

In particular, the mold of the compaction apparatus has a central longitudinal axis and at least one open end adapted for receiving the material sample to be compacted. More preferably, the mold has two opposing open ends. The compacting apparatus also preferably includes first and second pucks received within the open ends of the mold for confining therebetween the material to be compacted. The compression means preferably cooperates with the first puck for moving the first puck axially within the mold relative to the second puck to thereby apply an axial compressire force to the material confined within the mold between the pucks along an axis of compression substantially normal to the faces of the pucks. The shape of the pucks preferably approximates the shape defined by the interior of the mold so as to more completely confine the material sample therein.

The compression means of the material sample compacting apparatus preferably includes a ram mounted for movement into a first open end of the mold for compacting the material by applying a compresslye force, such as by compressire contact with the pucks, to the material sample along an axis of compression. The ram is preferably electrically actuated by an electric motor, such as by a stepper motor, and is operably mounted upon a frame such that it is constrained to axial movement. The drive means may be controlled manually or by control circuitry responsive to feedback signals, such as those indicative of the compression of the material sample. Alternatively, the ram may be hydraulically or mechanically actuated.

The base assembly of the compacting apparatus is positioned to support the second end of the mold as the axial compressire force is applied to the material sample confined therein. The base assembly preferably includes means for moving one end of the mold, preferably the second end, so that the central longitudinal axis of the mold moves from a neutral initial position in which the central longitudinal axis of the mold is collinear with the axis of compression to a tilted, operative position in which the central longitudinal axis of the mold is angularly offset from the axis of compression.

The means for moving also preferably revolves or orbits the center of the puck received by the second end of the mold about the axis of compression while the center of the first end of the mold is maintained substantially stationary once the mold is in the tilted operative position. This revolution gyrates the mold and, in combination with the axial compression, effectively compacts the confined material sample.

The base assembly of the compacting apparatus also preferably includes a turntable and a support platen adapted to carry the turntable and to allow for rotational movement therewith. The compacting apparatus also preferably includes a drive means operably connected to the support platen so as to rotate both the support platen and the turntable.

The support platen preferably includes means for mounting the turntable to the support platen for rotation of the support platen through a limited arc relative to the turntable so as to move the mold from an initial position in which the central longitudinal axis of the mold is collinear with the axis of compression to an operative position in which the central longitudinal axis of the mold is angularly offset from the axis of compression, thus tilting the mold.

During rotation through the limited arc, the turntable rotates about a predetermined axis of rotation which is parallel with and displaced from the axis of compression as the support platen rotates about an axis of gyratory rotation. The base assembly also includes means for rotating both the support platen and the turntable about the axis of a gyratory rotation following rotation of the turntable through the limited arc. The axis of gyratory rotation is collinear with the axis of compression and rotation of support platen and turntable thereabout revolves the center of the puck received by the second end of the mold about the axis of compression, thus effectively gyrating the tilted mold. The turntable preferably includes positioning means extending outwardly therefrom for receipt by an arcuate slot defined by the support platen; the combination of which defines the limited arc. The support platen also preferably includes axis offset means for controllably selecting the amount of angular offset of the central longitudinal axis of the mold from the axis of compression. The axis offset means preferably includes at least one adjustable stop positioned within the arcuate slot to select the circumferential length of the arcuate slot. The adjustable stop preferably includes at least one rod threadably inserted from a first end of the arcuate slot.

In an alternative embodiment, the adjustable stop preferably includes an annular plate overlying the support platen and having a projection extending therefrom for likewise adjusting the circumferential length of the arcuate slot. The adjustable stop incorporating the annular plate also preferably includes a stop positioning means operably connected to the annular plate for circumferentially rotating the annular plate in relation to the underlying support platen so as to position the projection of the annular plate within the arcuate slot. While the angle through which the slot extends may be varied to adjust the tilt imparted to the mold, the arcuate slot preferably extends the arcuate slot most preferably extends approximately 90° about the support platen.

The material sample compacting apparatus also preferably includes an outwardly extending flange carried by the second end of the mold. In addition, the base of the compacting apparatus preferably includes a plurality of circumferentially spaced rollers carried by the turntable and positioned for receiving and supporting the outwardly extending flange.

The material sample compacting apparatus also preferably includes a means for controlling the axial compresslye force supplied by the ram. The controlling means preferably includes means for measuring the axial compressire force applied to the material sample and most preferably includes a load cell for measuring the axial compressire force. The measurement of the axial compressive force is preferably provided to control circuitry which, in turn, preferably provides signals to the drive motor for adjusting the axial position of the ram and maintaining a substantially constant compressive force on the material sample.

BRIEF DESCRIPTION OF THE DRAWINGS

Some of the features and advantages of the invention having been described, others will become apparent from the detailed description which follows, and from the accompanying drawings, in which

FIGS. 5a to 10a correspond to FIGS. 5 to 10, respectively, and illustrate the orientation of the mold itself at various positions of operation;

DESCRIPTION OF THE PREFERRED EMBODIMENTS

The present invention will be described more fully hereinafter with reference to the accompanying drawings, in which a preferred embodiment of the invention is shown. This invention may, however, be embodied in many different forms and should not be construed as limited to the embodiments set forth herein; rather, these embodiments are provided so that this disclosure will be thorough and complete and will fully convey the scope of the invention to those skilled in the art.

Figures 1, 3, 4:
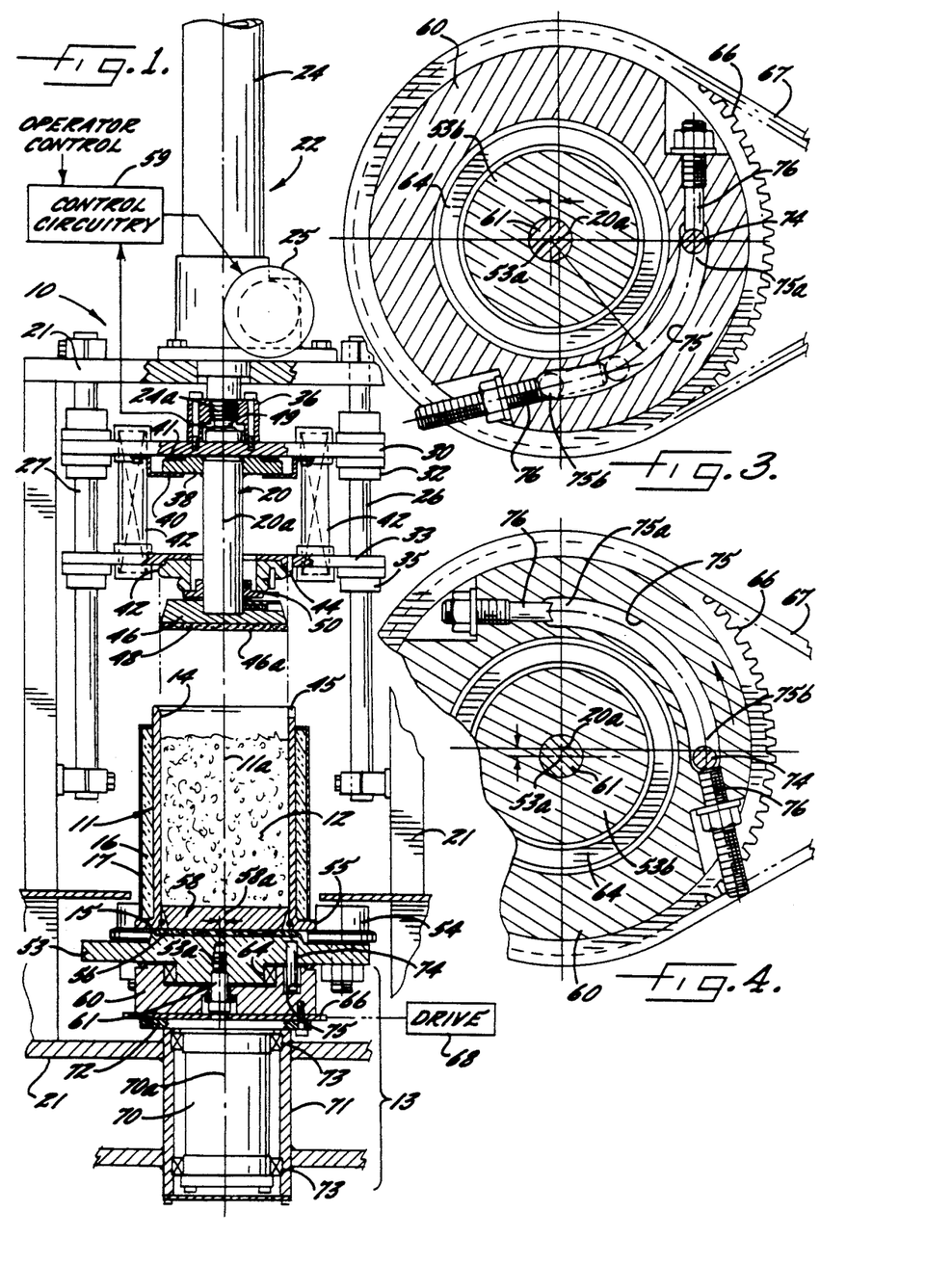
FIG. 1 is a front elevational view of a compacting apparatus of the present invention with a ram thereof in a raised position, and wherein portions of the apparatus are shown in cross-section for clarity of illustration.
FIG. 3 is a cross-sectional view through a portion of the compacting apparatus taking substantially along line 3—3 of FIG. 2 showing the apparatus in the initial neutral position.
FIG. 4 is a view similar to FIG. 3 subsequent to the rotation of the compacting apparatus illustrated in FIG. 2 into the tilted operative position.

Referring to FIG. 1, an apparatus 10 for compacting a sample of material, such as a loose sample of soil or paving material, for subsequent laboratory analysis of its physical properties is illustrated. The compacting apparatus 10 includes a mold 11 for receiving and confining the material sample 12 to be compacted, a compression means for axially compacting the confined material sample and a base assembly 13 for supporting and gyrating the mold 11 and its confined material sample. The mold 11, having a central longitudinal axis 11a, has at least one open end 14 for receiving the material sample 12 to be compacted. As illustrated in FIG. 1, the second opposite end 15 of the mold 11 may also be open. The mold 11 is preferably cylindrical and may suitably be surrounded by an insulating jacket 16 which, in turn, is encased in a cover jacket 17 to further protect the insulation. The insulating jacket 16 and cover jacket 17 decrease the heat loss from the material sample 12 so as to facilitate its compaction.

The compression means is preferably a ram 20 mounted for movement into the open first end 14 of the mold 11 for application of a compressive force to the material sample 12 confined in the mold 11 along an axis of compression 20a so as to compact the material. The ram 20 is carried by a frame 21 which restricts the ram 20 to axial movement. The ram 20 moves from an upper raised position illustrated in FIG. 1 to a lower position illustrated in FIG. 2 during the compaction of the material sample 12.

The ram's axial movement along the frame is preferably electrically controlled by a drive motor 25, such as an electric stepper motor. The drive motor 25 may be controlled manually or by means of control circuitry 59 responsive to feedback signals, such as those indicative of the compression of the material sample 12. Alternatively, the ram's axial movement may be controlled hydraulically or mechanically.

As shown in FIG. 1, the drive motor 25 is electromechanically connected to a ball screw jack which, in turn, controls the axial position of the ram 20. The ball screw jack 22 includes a housing 24 in which a jack screw 24a is slidably positioned.

The frame 21 preferably includes first and second parallel guide shafts 26, 27. The ram 20 is preferably slidably connected to both the first and second guide shafts 26, 27 for allowing axial movement of the ram 20 into the mold 11 during compaction of the material sample 12. Most preferably, the ram 20 is slidably connected to the first and second guide shaft 26, 27 by at least one upper slide plate 30 extending therebetween and connected to the ram 20. First and second apertures 31 are defined in the upper slide plate 30 for receiving the guide shafts 26, 27. As illustrated in FIG. 1, upper and lower slide collars 32 may be affixed to opposite faces of the upper slide plate 30 adjacent to the apertures 31 for facilitating the axial movement of the ram.

Preferably, a second spaced apart lower slide plate 33 is also mounted for travel along the first and second guide shafts 26, 27. The second slide plate 33 also has first and second apertures 34 defined therein for receiving the first and second guide shafts 26, 27. Slide collars 35 may be affixed to the lower slide plate 33 disposed adjacent to the apertures 34, as illustrated by the collars 35 affixed to the lower face 33a of the second slide plate 33 in FIGS. 1 and 2.

The upper plate 30 is operably connected to the jack screw 24a. As illustrated in FIG. 1, a shaft collar 36 may be affixed, such as by threaded fasteners 37, to an upper face 30a of the upper slide plate 30. The shaft collar 36 is, in turn, connected to the upper slide plate 30, such as by the threaded connection between an aperture defined in the shaft collar 36 and the jack screw 24a.

In addition, the ram 20 is attached to a lower face 30b of the upper slide plate 30. The ram 20 preferably includes an annular plate 38 affixed to a first end of the ram shaft 20. The ram 20 may thus be slidably attached to the upper slide plate 30 by an annular support ring 40 affixed at a first end to the lower face 30b of the upper slide plate 30 and having a second end extending under the annular plate 38 to secure the annular plate 38, and thus the ram 20, to the upper slide plate 30. The lateral distance between the annular support ring 40 is preferably such that the annular plate 38 is retained thereby while accommodating lateral movement of the ram shaft 20 to accommodate slight variances in positioning and tilt shift of the mold 11. A face bearing 41 is preferably disposed between the lower face 30b of the upper slide plate 30 and the annular plate 38 for facilitating relative rotational movement therebetween.

Figure 2:
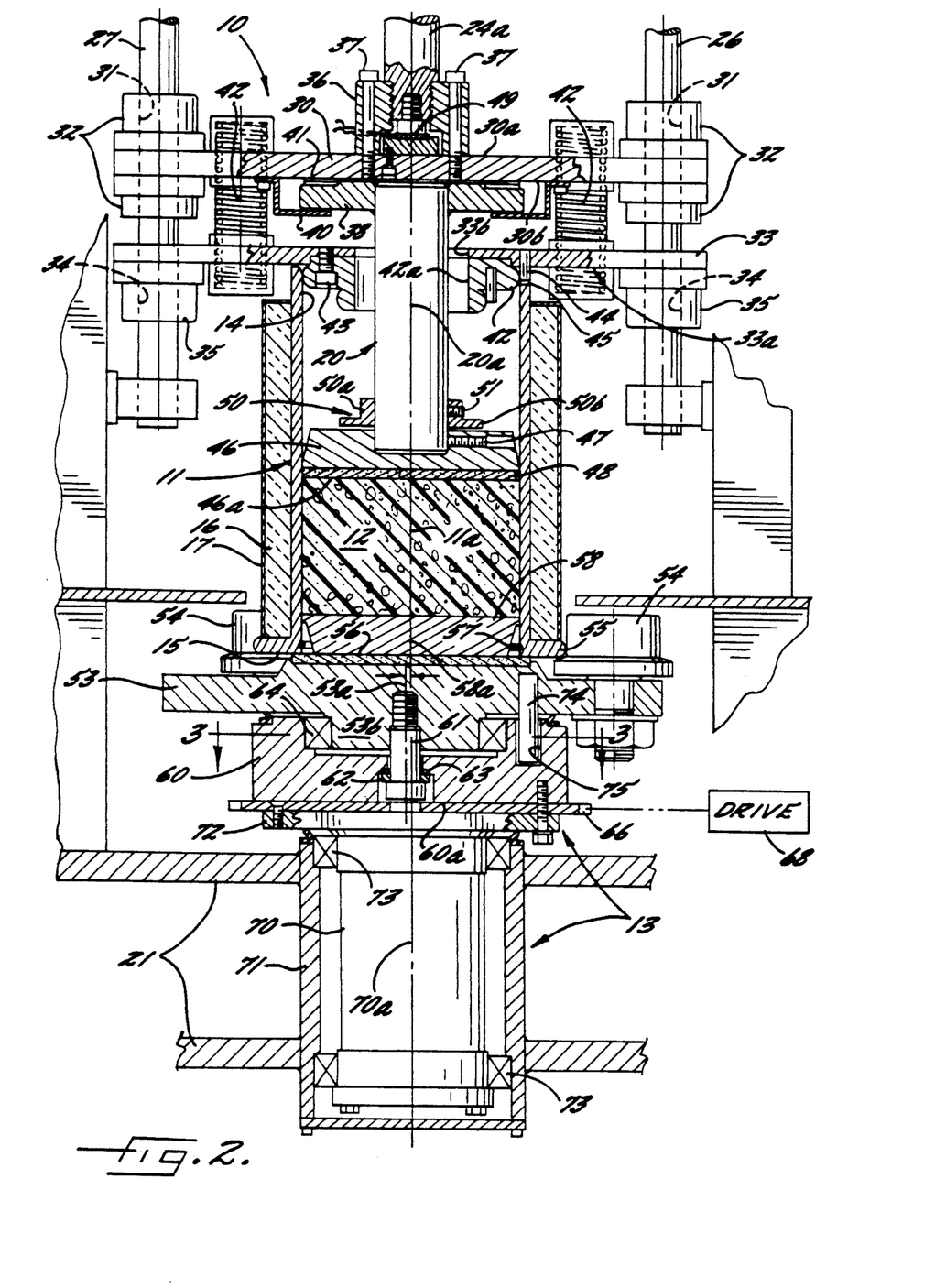
FIG. 2 is an enlarged detailed cross-sectional view of the compacting apparatus of FIG. 1, shown with the ram thereof in a lowered position.

The lower slide plate 33 and the upper slide plate 30 are biased apart by at least one, or more preferably two, springs 42. Thus, in the raised position of the compacting apparatus 10 as illustrated in FIG. 1, the upper slide plate 30 and the lower slide plate 33 are spaced apart. In contrast, the upper slide plate 30 and the lower slide plate 33 are relatively closely spaced in the lowered compacting position of the compacting apparatus 10 as shown in FIG. 2.

The lower slide plate 33 has a central aperture 33b defined therein for receiving the ram shaft 20. The diameter of the central aperture 33b of the second plate 33 is relatively large in comparison with the diameter of the ram shaft 20, thus permitting limited lateral movement of the ram shaft 20 to accommodate variations in the initial position of the mold 11 and lateral movements during operation.

In addition, a mold locating means, preferably an annular ring 42, is affixed, such as by a threaded fastener 43, to the lower face 33a of the lower slide plate 33. As best illustrated in FIG. 2, the exterior shape of the annular mold locating ring 42 preferably approximates the interior shape of the mold 11 such that the mold locating ring 42 snugly fits within the mold 11, thus retaining the open first end 14 of mold 11 about the centerline 20a of the ram shaft 20. The mold locating ring 42 also defines a center aperture 42a positioned substantially concentrically with the center aperture 33b of the lower slide plate 33 for receiving the ram shaft 20. The center aperture 42a of the mold locating ring 42 preferably has a diameter at least as large as that of the center aperture 33b of the lower slide plate 33.

A locating means, preferably a pin 44, is carried by the lower slide plate 33 and extends outwardly therefrom. In addition, a sidewall of the first end 14 of the mold has a longitudinal slot 45 defined therein for receiving the locating means. The combination of the locating means and the longitudinal slot 45 facilitates the alignment of the lower slide plate 33, and therefore the ram 20, with the mold 11. This combination also prevents the mold 11 from rotating during its gyration.

A second end of the ram shaft 20 is preferably operably connected to a compaction puck 46, such as by set screws 47 as illustrated in FIG. 1. The lateral edges of the compaction puck 46 are preferably tapered to accommodate slight tilting of the mold 11 relative to the ram 20 during the gyration of the material sample 12. A lower face 46a of the puck 46 preferably has a ceramic disk 48 affixed thereto. The ceramic disk 48 contacts the material sample 12 and protects the puck 46 from excessive abrasion through repeated contact therewith. In addition, the ceramic disk 48 provides additional insulation so as to decrease heat loss from the material sample 12 during compaction.

A ram shaft collar 50 is also preferably disposed about the ram shaft 20 adjacent an upper face 46b of the puck 46. The ram shaft collar 50 is affixed to the second end of the ram shaft 20, such as by set screws 51 as illustrated in FIGS. 1 and 2, and has a stepped outer diameter. Thus, a first portion 50a of the ram shaft collar 50 has a relatively small diameter so as to fit within the center aperture 42a of the mold locating ring 42. A second portion 50b of the ram shaft collar 50, however, has a larger diameter than that of the center aperture 42a of the mold locating ring 42 so as to contact the mold locating ring 42. The ram shaft collar 50, thus, supports the mold locating ring 42 and the lower slide plate 33 while the ram 20 is in a raised position as illustrated in FIG. 1.

The compacting apparatus 10 also preferably includes a means for controlling the axial compressive force applied by the ram 20. This controlling means preferably includes means for measuring the axial compressive force applied to the material sample 12, such as a load cell 49 as illustrated in FIG. 1. The load cell 49 is preferably positioned colinearly with the jack screw 24a and the ram shaft 20 within the shaft collar 36. The load cell 49, thus, measures the axial compressive force applied to the material sample 12 by the ram 20 and may provide signals to control circuitry 59 which, in turn, may control the drive motor 25 such that a substantially constant amount of axial compressive force is preferably applied to the material sample 12.

Figures 5, 6, 7:
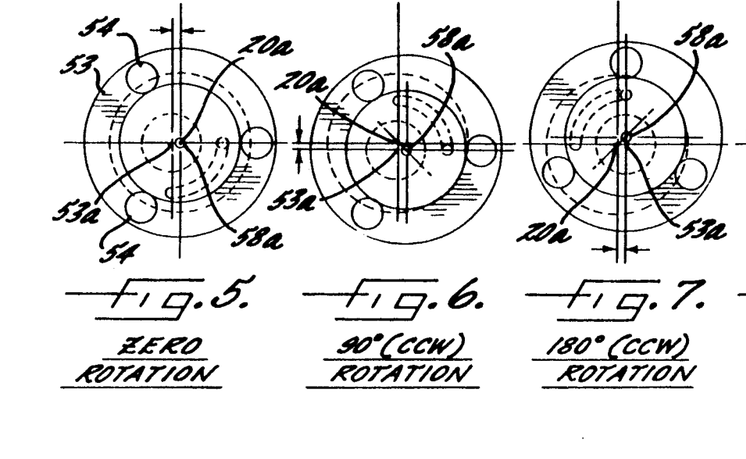
FIGS. 5 to 10 are schematic plan views of a rotating mold and base of a compacting apparatus of the present invention at various positions of operation.
Figures 5A, 6A:
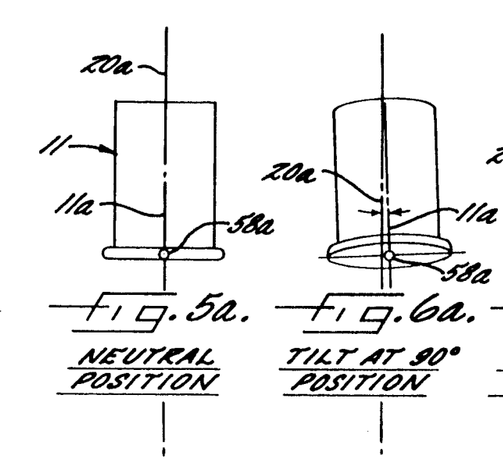
Figure 7A:
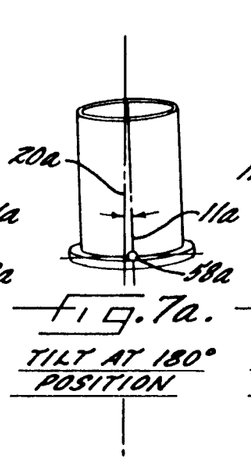
Figure 8:
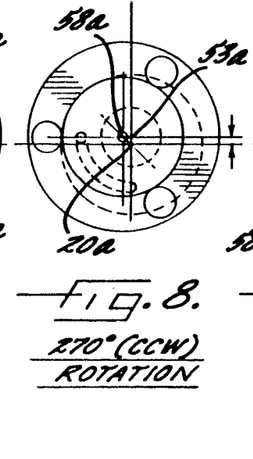
Figure 8A:
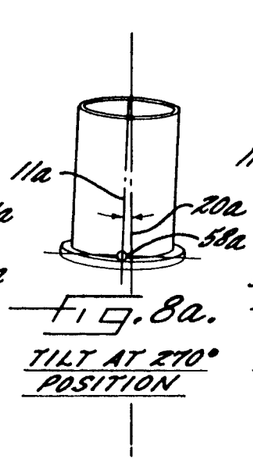
Figures 9, 10:
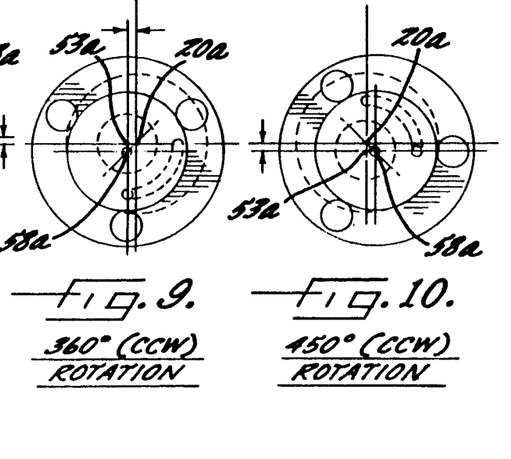
Figures 9A, 10A:
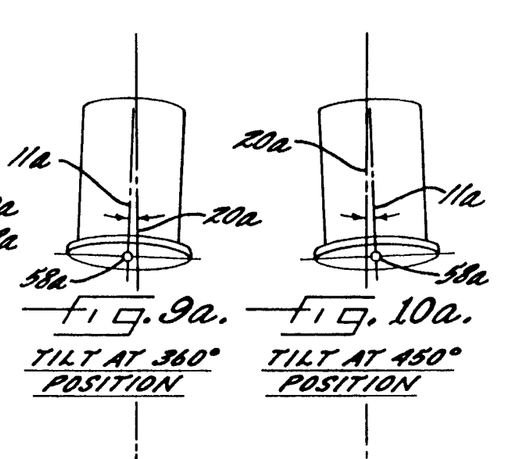

The second end 15 of the mold 11 is supported by a base assembly 13. In one embodiment of the present invention, a mold bottom puck 58 is received by the second end 15 of the mold 11 as illustrated in FIGS. 1 and 2. The base assembly 13 also preferably includes a means for moving the second end 15 of the mold 11 so that the central longitudinal axis 11a of the mold 11 is shifted from an initial neutral position to a tilted operative position. The initial neutral position is illustrated in both FIGS. 1, 2 and 5 in which the central longitudinal axis 11a of the mold 11 is collinear with the axis 20a of ram shaft 20, which defines the axis of compression. In contrast, the tilted operative position is illustrated in FIG. 6 in which the central longitudinal axis 11a of the mold 11 is angularly offset from the axis of compression 20a. Once in the tilted operative position, the base assembly 13 may be moved relative to the mold 11 as shown in FIGS. 7-10 such that the center of the mold bottom puck 58a revolves or orbits about the axis of compression 20a at the second end 15 while the center of the first end 14 is maintained substantially coincident with the axis of compression 20a.

Furthermore, the base assembly 13 includes a turntable 53 and means for supporting the second end 15 of the mold 11 so as to permit relative movement of the turntable 53 therebeneath. The supporting means preferably comprise a plurality of rollers 54 circumferentially spaced about the second end 15 of the mold 11 and carried by the turntable 53. In addition, the second end 15 of the mold 11 preferably includes an outwardly extending flange 55. The circumferentially spaced rollers 54 are preferably positioned to receive and support the outwardly extending flange 55.

As shown in FIGS. 1 and 2, a second ceramic disk 56 is preferably positioned between the turntable 53 and the mold bottom puck 58 for facilitating the relative movement between the turntable 53 and the second end 15 of the mold 11 and for decreasing the heat loss of the material sample 12 during compaction. A retainer ring 57 is preferably inserted and held in the interior surface of the second end 15 of the mold 11. The retainer ring 57 supports and retains the tapered mold bottom puck 58 for limited axial movement.

The base assembly 13 also preferably includes a support platen 60 which carries the turntable 53. Furthermore, the base assembly 13 preferably includes means for mounting the turntable 53 to the support platen 60. The means for mounting allows rotation of the turntable 53 through a limited arc so as to move the second end 15 of the mold 11 from the initial neutral position to the tilted operative position. The mounting means preferably includes a threaded stud 61 inserted from an aperture defined in the support platen 60 to the turntable 53 for permitting rotation thereabout. The threaded stud 61 and a plurality of bearings 64 define the predetermined axis of rotation 53a of the turntable 53 during rotation through the limited arc to be parallel to and displaced from the axis of compression 20a. In addition, a wear ring 62 and thrust bearing 63 may be interposed between the threaded stud 61 and the support platen 60 for facilitating rotation thereabout and for decreasing deterioration thereof.

As shown in FIG. 2, the turntable 53 is preferably carried by the support platen 60 by means of a center hub 53b extending downwardly from the turntable 53 for receipt by a central indention in the support platen 60. The plurality of bearings 64, preferably tapered bearings, are positioned about the periphery of the center hub 53b of the turntable 53. The bearings 64 are positioned within a race defined by the opposing sidewalls of the center hub 53b of the turntable 53 and the center indention of the support platen 60.

A drive means is operably connected to the base assembly 13, and more preferably is connected to the support platen 60 for rotating the support platen 60. Most preferably, the drive means includes a sprocket 66 axially aligned with and having a first face affixed to a lower face 53a of the support platen 60. As shown in FIG. 3, the sprocket 66 has a number of teeth circumferentially spaced about its periphery for receiving and meshing with a drive chain 67. The drive chain 67 is, in turn, operably connected to a suitable drive 68 for advancing the drive chain 67 so as to rotate the sprocket 66.

A second face of the sprocket 66 is affixed to and supported by a gyratory support shaft 70 for further supporting the mold. The gyratory support shaft 70 is mounted for rotation within a support housing 71 about an axis of gyratory rotation 70a collinear with the axis of compression 20a. The gyratory support shaft 70 preferably has a mounting plate 72 affixed to a first end thereof for affixation with the drive sprocket 66 and the support platen 60 as illustrated in FIG. 1. The rotational movement of the gyratory support shaft 70 is facilitated by a plurality of bearings 73, preferably tapered bearings, positioned about the periphery of the gyratory support shaft 70 in races defined between the gyratory support shaft 70 and the housing 71 thereabout. The housing 71 of the gyratory support shaft 70 may, in turn, be connected to a lower portion of the frame 21 such that the relative positions of the ram 20 and the mold 11 and the movement therebetween is controlled.

In operation, the mold 11 is loaded with a material sample 12 while in an initial neutral position as shown in FIG. 1 wherein the central longitudinal axis 11a of the mold 11 is collinear with the axis of compression 20a. Additionally, the centers of both the first end 14 and the mold bottom puck 58 are coincident with the central longitudinal axis 11a of the mold 11 and the axis of compression 20a. Subsequently, the ram 20 is lowered into the first end 14 of the mold 11 so as to axially compress the confined material sample 12 as illustrated in FIG. 2. In order to more closely simulate the kneading effect imparted by the rolling of vehicle tires or other compacting devices over asphalt or other paving materials, the mold 11 is subsequently tilted and gyrated while the material sample 12 is continually compressed.

The tilting of the mold 11 is provided by the means for mounting the turntable 53 to the support platen 60 which allows the turntable 53 to rotate through a limited arc about the predetermined axis of rotation 53a as the support platen 60 rotates about the axis of gyratory rotation 70a prior to engaging the turntable 53 for rotation therewith. This limited initial rotation by the turntable 53 is preferably provided by the combination of a projection 74, such as a dowel rod, outwardly extending from the turntable 53 in an arcuate slot 75 defined by the support platen 60 for receiving the outwardly extending projection 74 of the turntable 53. Most preferably, the arcuate slot 75 is centered about the predetermined axis of rotation 53a. In the initial neutral position, the projection 74 is located at a first end 75a of the arcuate slot 75.

In order to tilt the mold, the support platen 60 is rotated by the drive 68. During the initial rotation of the support platen 60 about the axis of gyratory rotation 70a, the turntable 53 remains substantially rotationally stationary relative to the axis of gyratory rotation 70a as the arcuate slot 75 moves relative to the projection 74. The arcuate slot moves from an initial position illustrated in FIG. 3 in which the projection is located at the first end 75a of the slot 75 to a final position shown in FIG. 4 in which the projection 74 is in engagement with the second end 75b of the slot 75. This movement of the turntable 53 about the predetermined axis of rotation 53a relative to the support platen 60 and the movement of the arcuate slot 75 relative to the projection 74 gradually laterally shifts the center of the mold bottom puck 58a and therefore the second end 15 of the mold 11 relative to the axis of compression 20a. The lateral shifting of the second end 15 of the mold 11 effectively tilts the mold 11 as the center of the first end 14 of the mold 11 is maintained substantially coincident with the axis of compression 20a due to the positioning of the annular ring 42 within the mold 11.

The degree of tilt of the mold 11 and thus the angular offset between the central longitudinal axis 11a of the mold 11 and the axis of compression 20a is defined by the length of the arcuate slot 75 in the support platen 60 and the amount of lateral displacement between the axis of compression 20a and the predetermined axis of rotation 53a.

Although the arcuate slot 75 may extend through any desired angle, the slot 75 preferably extends at least 90° about the support platen 60. As shown in FIGS. 3 and 4, the length of an arcuate slot 75 in the support platen 60 may be adjusted by means of an adjustable stop 76 positioned at one end of the slot. The adjustable stop 76 may be threadably engaged within the support platen 60 and positioned such that it extends within the arcuate slot 75 so as to limit the circumferential length of the arcuate slot 75. As illustrated in FIGS. 3 and 4, adjustable stops 76 may be positioned at both ends of the arcuate slot 75 for additional control over the degree of tilt of the mold 11. The adjustable stop 76 positioned at the first end 75a of the arcuate slot 75 provides fine control over the alignment of the center longitudinal axis 11a of the mold 11 with the axis of compression 20a in the initial neutral position.

The amount by which an adjustable stop, such as a threaded rod, may enter the arcuate slot 75 and thus limit its circumferential length is limited due to the eventual contact of a substantially linear rod with a curved sidewall of the arcuate slot 75.

Figures 11, 12:
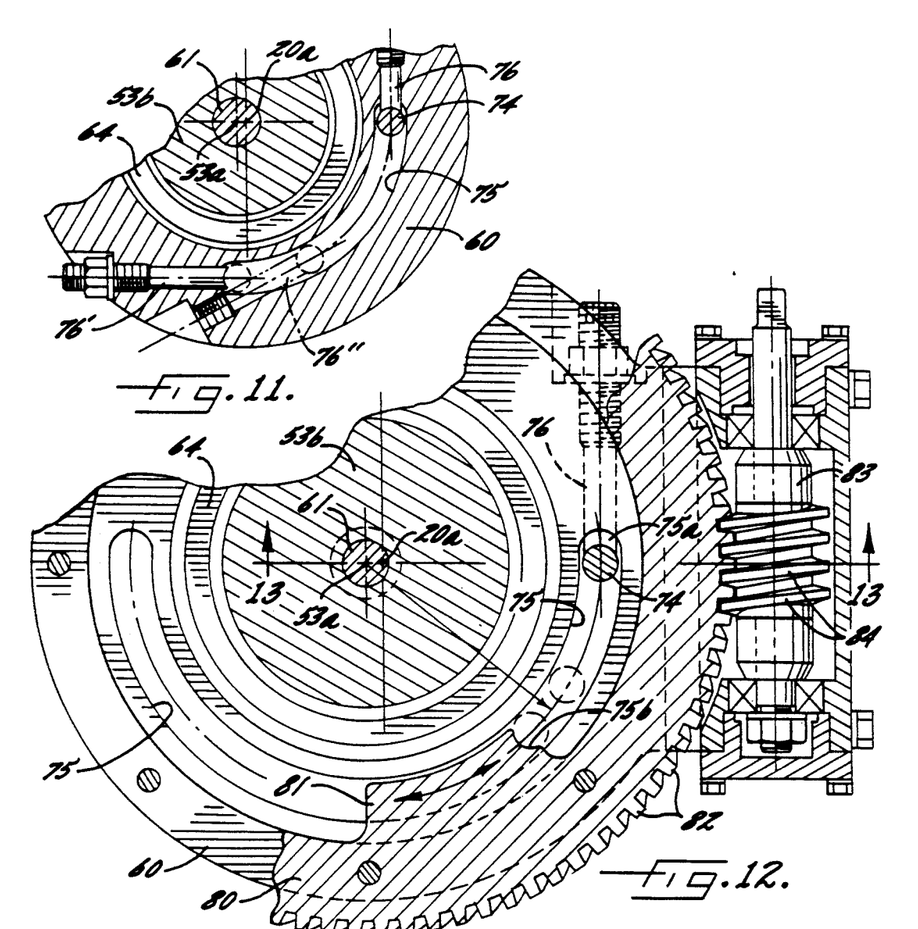
FIG. 11 is a fragmentary cross-sectional view similar to FIG. 3 but illustrating an alternate embodiment of the base of a compacting apparatus.
FIG. 12 is a fragmentary cross-sectional view illustrating still another alternate form of the base of a compacting apparatus.

In an alternative embodiment illustrated in FIG. 11, a plurality of adjustable stops 76' and 76", preferably threaded rods, may be positioned along the arcuate slot 75 so as to be inserted therein at various locations. By selectably inserting a particular threaded rod into the arcuate slot 75, additional control is provided over the circumferential length of the slot 75. Thus, insertion of stop 76" as shown in FIG. 11 provides for a shorter slot than does insertion of stop 76'.

Figure 13:
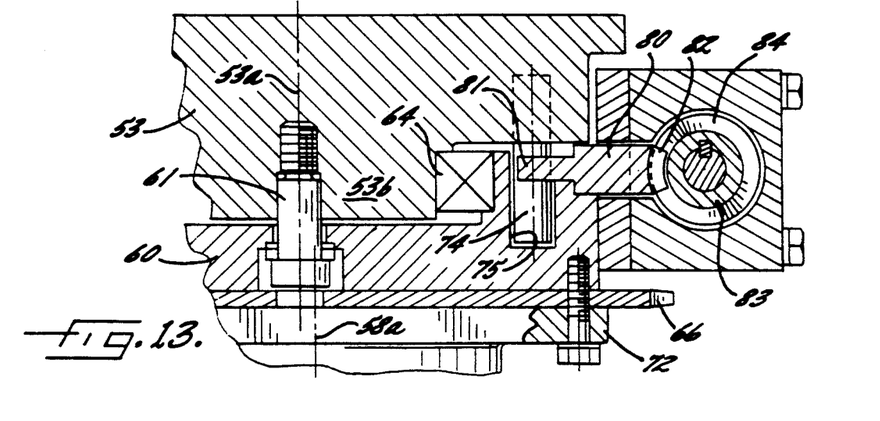
FIG. 13 is a cross-sectional view of the embodiment of the compacting apparatus illustrated in FIG. 12 taken substantially along line 13—13 of FIG. 12.

In still another alternative embodiment, an adjustable stop includes an annular plate 80 overlying the support platen 60 as illustrated in FIGS. 12 and 13. By adjusting the position of this embodiment of the adjustable stop, the angular offset between the central longitudinal axis 11a of the mold 11 and the axis of compression 20a is accordingly varied. The annular plate 80 has a projection 81 extending over the arcuate slot 75 so as to engage the outwardly extending projection 74 of the turntable 53 and form the second end 75b of the elongated arcuate slot 75. The annular plate 80 also preferably includes a positioning means for selectively locating the projection 81 relative to the arcuate slot 75 of the support platen 60. Most preferably, the periphery of the annular plate 80 forms a worm gear which includes a plurality of spaced apart teeth 82 and the positioning means includes a threaded rod 83 whose raised threads 84 intersect and mesh with the plurality of teeth 82 of the annular plate 80. Thus, by rotating the threaded rod 83 of the positioning means, the annular plate 80 may be rotated relative to the support platen 60 so as to selectively adjust the circumferential length of the arcuate slot 76 therein.

Therefore, to tilt the mold 11 to its operative position, the turntable 53 is rotated about the predetermined axis of rotation 53a relative to the support platen 60. Due to the rotation of the turntable 53, the arcuate slot 75 in the support platen 60 moves relative to the projection 74 extending outwardly from the turntable 53 from the initial position as shown in FIGS. 3 and 5 to the final position as shown in FIGS. 4 and 6.

Further rotation of the support platen 60 by the drive 68 also rotates the turntable 53 due to the engagement of the outwardly extending projection 74 of the turntable 53 with the second end 75b of the arcuate slot 75. This further rotation of both the support platen 60 and the turntable 53 is about the axis of gyratory rotation 70a which is collinear with the axis of compression 20a.

As illustrated in FIGS. 7–10 and corresponding FIGS. 7a–10a, the resultant revolution of the support platen 60 and turntable 53 about the axis of gyratory rotation 70a moves the turntable 53 and thus the circumferentially spaced rollers 54 carried thereon relative to the second end 15 of the mold 11. Thus, the center of the mold bottom puck 58a revolves about the axis of compression 20a at the angular offset defined between the axis of compression 20a and the central longitudinal axis 11a of the mold 11. During this revolution, the center of the first end 14 of the mold 11 is maintained substantially coincident with the axis of compression 20a.

This revolution of the center of the mold bottom puck 58a about the axis of compression 20a effectively gyrates the mold 11. In addition, the axial compresslye force is simultaneously applied. The combination of the gyration and the axial compression effectively kneads the material sample 12 so as to simulate the effect of a compaction device or vehicle rolling thereover.

Once the material sample 12 is sufficiently gyrated, the mold 11 may be returned to its initial neutral position by reversing the direction of rotation of the support platen 60. This reversal moves the arcuate slot 75 relative to the outwardly extending projection 74 of the turntable 53 from the final position shown in FIG. 4 to the initial position shown in FIG. 3. While FIGS. 5-10 and corresponding 5a-10a depict counterclockwise rotation of the mold 11 during gyration, clockwise rotation is equally applicable.

In the drawings and specification, there have been disclosed typical preferred embodiments of the invention and, although specific terms are employed, they are used in a generic and descriptive sense only and not for purposes of limitation, the scope of the invention being set forth in the following claims:

That which is claimed is:

1. A compactor apparatus comprising:
   a cylindrical mold having a central longitudinal axis and a first open end for receiving material to be compacted;
   a ram mounted for movement into the first open end of said mold for applying a compressire force to the material in the mold along an axis of compression to compact the material; and
   a base positioned to support a second end of said mold as the axial compressire force is applied thereto;
   said base including means for moving said second end of the mold so that the central longitudinal axis of the mold moves from an initial neutral position in which the central longitudinal axis of the mold is collinear with the axis of compression to a tilted operative position in which the central longitudinal axis of the mold is angularly offset from the axis of compression and orbits thereabout at said second end of said mold.

2. The compactor apparatus according to claim 1 wherein said base additionally includes a support platen and a turntable carried by said support platen, said compactor apparatus also including means for mounting said turntable to said support platen for rotation of the turntable, relative to the support platen, through a limited arc about an axis of rotation parallel with and displaced from the axis of compression so as to move said mold from an initial neutral position in which the central longitudinal axis of the mold is collinear with said axis of compression to a tilted operative position in which the central longitudinal axis of the mold is angularly offset from said axis of compression.

3. The compactor apparatus according to claim 2 wherein said base additionally includes means for rotating both said support platen and said turntable about an axis of gyratory rotation following said rotation of said turntable through said limited arc, said axis of gyratory rotation being collinear with said axis of compression such that rotation thereabout revolves said second end of said mold about said axis of compression.

4. The compactor apparatus according to claim 2 wherein said turntable includes positioning means extending outwardly therefrom and wherein said support platen defines an arcuate slot therein for receiving said positioning means.

5. The compactor apparatus according to claim 4 wherein said support platen additionally includes axis offset means for selecting the amount of offset of said central longitudinal axis of the mold from the axis of compression.

6. The compactor apparatus according to claim 5 wherein said axis offset means includes at least one adjustable stop positioned within said arcuate slot so as to select the circumferential length of said arcuate slot.

7. The compactor apparatus according to claim 6 wherein said adjustable stop includes at least one rod threadably inserted from a first end of said arcuate slot.

8. The compactor apparatus according to claim 6 wherein said adjustable stop includes an annular plate overlying said support platen and having a projection extending therefrom for adjusting the circumferential length of the arcuate slot.

9. The compactor apparatus according to claim 8 wherein said adjustable stop additionally includes a stop positioning means operably connected to said annular plate for circumferentially rotating said annular plate relative to said underlying support platen so as to position said projection within said arcuate slot.

10. The compactor apparatus according to claim 6 wherein said arcuate slot extends at least 90° about said support platen.

11. The compactor apparatus according to claim 2 further comprising an out-turned flange carried by said second end of said mold and wherein said means for supporting said second end of said mold comprises a plurality of circumferentially spaced rollers carried by said turntable and positioned for receiving and supporting said out-turned flange.

12. The compactor apparatus according to claim 2 further comprising a drive means operably connected to said support platen to rotate said support platen.

13. The compactor apparatus according to claim 1 further comprising a means for controlling the axial compressive force applied by said ram.

14. The compactor apparatus according to claim 13 wherein said means for controlling the axial compressive force includes a means for measuring the axial compressive force applied to the material.

15. The compactor apparatus according to claim 14 further comprising means for axially translating said ram within said mold.

16. The compactor apparatus according to claim 15 wherein said axial translation means is an electric motor, said compactor apparatus further comprising control circuitry responsive to said measuring means for controlling the axial translation of said ram provided by said electric motor.

17. The compactor apparatus according to claim 1 wherein said ram includes a substantially circular puck affixed to a first end thereof for contacting said material, said puck having a diameter approximately equal to the interior diameter of said cylindrical mold.

18. An apparatus for compacting material comprising:
   a mold having a central longitudinal axis and open opposite ends adapted for receiving material to be compacted;
   first and second pucks received within said mold for confining therebetween the material to be compacted;
   compression means mounted for movement into an open first end of said mold and cooperating with said first puck for moving said first puck axially within said mold relative to said second puck and thereby applying an axial compressire force to the material confined within the mold between the pucks along an axis of compression normal to the faces of the pucks; and a base positioned to support a second end of said mold, said base including means for moving said second end of said mold so that the central longitudinal axis of the mold moves from an initial neutral position in which the central longitudinal axis of the mold is collinear with the axis of compression to a tilted operative position in which the central longitudinal axis of the mold is angularly displaced from the axis of compression and orbits thereabout at said second end of said mold.

19. The apparatus for compacting material according to claim 18 wherein said base additionally includes a support platen and a turntable carried by said support platen, said apparatus for compacting material also including means for mounting said turntable to said support platen for rotation of the turntable, relative to the support platen, through a limited arc about an axis of rotation parallel with and displaced from the axis of compression so as to move said mold from an initial neutral position in which the central longitudinal axis of the mold is collinear with said axis of compression to a tilted operative position in which the central longitudinal axis of the mold is angularly offset from said axis of compression.

20. The apparatus for compacting material according to claim 19 wherein said base additionally includes means for rotating both said support platen and said turntable about an axis of gyratory rotation following said rotation of said turntable through said limited arc, said axis of gyratory rotation being collinear with said axis of compression such that rotation thereabout revolves said second end of said mold about said axis of compression.

21. The apparatus for compacting material according to claim 19 wherein said turntable includes positioning means extending outwardly therefrom and wherein said support platen defines an arcuate slot therein for receiving said positioning means.

22. The apparatus for compacting material according to claim 21 wherein said support platen additionally includes axis offset means for controllably selecting the amount of offset of said axis of compression from the central longitudinal axis of the mold.

23. The apparatus for compacting material according to claim 22 wherein said axis offset means includes at least one adjustable stop positioned within said arcuate slot so as to select the circumferential length of said arcuate slot.

24. The apparatus for compacting material according to claim 23 wherein said adjustable stop includes at least one rod threadably inserted from a first end of said arcuate slot.

25. The apparatus for compacting material according to claim 23 wherein said adjustable stop includes an annular plate overlying said support platen and having a projection extending therefrom for adjusting the circumferential length of the arcuate slot.

26. The apparatus for compacting material according to claim 25 wherein said adjustable stop additionally includes a stop positioning means operably connected to said annular plate for circumferentially rotating said annular plate in relation to said underlying support platen so as to position said projection within said arcuate slot.

27. The apparatus for compacting material according to claim 19 further comprising a drive means operably connected to said support platen so as to rotate both said support platen and said turntable about said axis of rotation.

28. The apparatus for compacting material according to claim 19 including an outwardly extending flange carried by said second end of said mold and wherein said means for supporting said second end of said mold comprises a plurality of circumferentially spaced rollers carried by said turntable and positioned for receiving and supporting said outwardly extending flange.

29. The apparatus for compacting material according to claim 18 further comprising a means for controlling the axial compressire force applied by said ram.

30. The apparatus for compacting material according to claim 29 wherein said means for controlling the axial compresslye force includes a means for measuring the axial compressire force applied to the material.

31. The compactor apparatus according to claim 30 further comprising means for axially translating said ram within said mold.

32. The apparatus for compacting material according to claim 31 wherein said axial translation means is an electric motor, said compactor apparatus further comprising control circuitry responsive to said measuring means for controlling the axial translation of said ram provided by said electric motor.

33. The apparatus for compacting material according to claim 32 wherein said axial translation means is an electric motor, said compactor apparatus further comprising control circuitry responsive to said measuring means for controlling the axial translation of said ram provided by said electric motor.

34. An apparatus for compacting material comprising:
a mold having a central longitudinal axis and a first open end for receiving material to be compacted;
compression means for movement into said first open end of said mold for applying compressive force to the material in the mold along an axis of compression to compact the material;
a turntable carrying a second end of said mold; and
a support platen carrying said turntable and mounted for rotation of the turntable, relative to the support platen, through a limited arc about an axis of rotation parallel to and displaced from the axis of compression so as to move said mold from an initial neutral position in which the central longitudinal axis of the mold is collinear with said axis of compression to a tilted operative position in which the central longitudinal axis of the mold is angularly offset from said axis of compression.

35. The apparatus for compacting material according to claim 34 further comprising means for rotating both said support platen and said turntable about an axis of gyratory rotation following said rotation of said turntable through said limited arc, said axis of gyratory rotation being collinear with said axis of compression such that rotation thereabout revolves said second end of said mold about said axis of compression.

36. An apparatus for compacting material according to claim 34 wherein said turntable includes positioning means extending outwardly therefrom and wherein said support platen defines an arcuate slot therein for receiving said positioning means.

37. An apparatus for compacting material according to claim 36 wherein said support platen additionally includes axis offset means for controllably selecting the amount of offset of said predetermined axis from the axis of the mold.

38. An apparatus for compacting material according to claim 37 said axis offset means includes at least one adjustable stop positioned within said arcuate slot so as to select the circumferential length of said arcuate slot.

39. An apparatus for compacting material according to claim 34 further comprising a drive means operably connected to said support platen so as to rotate both said support platen and said turntable about said axis of rotation.

40. An apparatus for compacting material according to claim 34 including an outwardly extending flange carried by said second end of said mold and means for supporting said second end of said mold carried by said turntable, said supporting means comprising a plurality of circumferentially spaced rollers positioned for receiving and supporting said outwardly extending flange.

41. A method for compacting a material comprising the steps of:
 placing the material in a first open end of a mold, said mold having a central longitudinal axis therethrough;
 compressing said material from the first end of said mold along an axis of compression;
 supporting a second end of said mold during said axial compression;
 shifting said second end of said mold so that the central longitudinal axis of the mold moves from an initial neutral position in which the central longitudinal axis of the mold is collinear with the axis of compression to a tilted operative position in which the central longitudinal axis of the mold is angularly offset from the axis of compression; and
 moving said second end of said mold such that said central longitudinal axis of the mold orbits about said axis of compression at said second end of said mold while maintaining the angular offset established therebetween by the shifting step.

42. The compacting method according to claim 41 wherein said supporting step comprises the step of supporting the second end of said mold with a plurality of rollers circumferentially spaced about the second end of said mold and said moving step comprises the step of rotating all of said circumferentially spaced rollers about an axis of gyratory rotation, said axis of gyratory rotation being collinear with the axis of compression.

43. The compacting method according to claim 41 further comprising the step of selectably adjusting the angular offset established between the central longitudinal axis of the mold and the axis of compression by the shifting step.

44. The compacting method according to claim 41 further comprising the step of controlling the amount of compression of said material during said compressing step.

45. The compacting method according to claim 44 wherein said controlling step includes the step of measuring the amount of compression of said material.

46. The compacting method according to claim 41 further comprising the step of maintaining a substantially constant amount of compression on said material.

* * * * *

UNITED STATES PATENT AND TRADEMARK OFFICE
CERTIFICATE OF CORRECTION

PATENT NO. : 5,323,655
DATED : June 28, 1994
INVENTOR(S) : John T. Eagan et al.

It is certified that error appears in the above-identified patent and that said Letters Patent is hereby corrected as shown below:

On the face of the patent, Section [56], the reference listed as:

"Formulation des enrobés Bilan des essais à la presse à cisaillement giratoire (PCG)," *Bitumes et enrobes bitumineux*, pp. 13-21" should be:

-- Formulation des enrobés Bilan des essais à la presse à cisaillement giratoire (PCG)," *Bitumes et enrobés bitumineux*, pp. 13-21 --.

On the face of the patent (page 2), Section [56], the reference listed as:

"Press designed to study the compactness of bituminous mixes," *Gyrtory Shear Compacting Press*, Materials des Laboratories des Ponts Chaussees, 2 page brochure" should be:

-- Press designed to study the compactness of bituminous mixes," *Gyrtory Shear Compacting Press*, Materials des Laboratoires des Ponts Chaussees, 2 page brochure --.

In the Abstract, lines 5 and 8-9, "compressire" should be -- compressive --.

Column 1, line 14, "compressire" should be -- compressive --.

Column 1, line 23, "hamer" should be -- hammer --.

UNITED STATES PATENT AND TRADEMARK OFFICE
CERTIFICATE OF CORRECTION

PATENT NO. : 5,323,655

DATED : June 28, 1994

INVENTOR(S) : John T. Eagan et al.

It is certified that error appears in the above-identified patent and that said Letters Patent is hereby corrected as shown below:

Column 2, line 43 "Compresslye" should be --Compressive--.

Column 2, line 44, "compressire" should be -- compressive --.

Column 2, line 56, "compressire" should be -- compressive --.

Column 3, line 58, "preferably extends the arcuate slot" should be deleted.

Columns 3 and 4, lines 68 and 1, "compresslye" should be -- compressive --.

Column 4, line 3, "compressire" should be -- compressive --.

Column 4, line 5, "compressire" should be -- compressive --.

Column 4, line 23, after "ram" delete the period ".".

Column 4, line 25, "taking" should be -- taken --.

Column 5, line 11, "compressire" should be -- compressive --.

Column 7, line 13, "compressire" should be -- compressive --.

Column 7, line 18, "colinearly" should be -- collinearly --.

UNITED STATES PATENT AND TRADEMARK OFFICE
CERTIFICATE OF CORRECTION

PATENT NO. : 5,323,655

DATED : June 28, 1994

INVENTOR(S) : John T. Eagan et al.

It is certified that error appears in the above-identified patent and that said Letters Patent is hereby corrected as shown below:

Column 7, line 20, "compressire" should be -- compressive --.

Column 10, line 68, "compresslye" should be -- compressive --.

Column 11, line 12, before "5a-10a" insert -- FIGS. --.

Column 11, line 27, "compressire" should be -- compressive --.

Column 11, line 31, "compressire" should be -- compressive --.

Column 12, line 68, "compressire" should be -- compressive --.

Column 14, line 15, "compressire" should be -- compressive --.

UNITED STATES PATENT AND TRADEMARK OFFICE
CERTIFICATE OF CORRECTION

PATENT NO. : 5,323,655

DATED : June 28, 1994

INVENTOR(S) : John T. Eagan et al.

It is certified that error appears in the above-identified patent and that said Letters Patent is hereby corrected as shown below:

Column 14, line 18, "compresslye" should be -- compressive --.

Column 14, line 19, "compressire" should be -- compressive --.

Column 15, line 5, after "37" insert -- wherein --.

Signed and Sealed this

Twenty-second Day of November, 1994

Attest:

BRUCE LEHMAN

*Attesting Officer*  *Commissioner of Patents and Trademarks*